(12) United States Patent
Shiber

(10) Patent No.: US 6,482,215 B1
(45) Date of Patent: Nov. 19, 2002

(54) ADJUSTABLE VESSEL CLEANER AND METHOD

(76) Inventor: Samuel Shiber, 365 Kearney Cir., Manchester, NH (US) 03104

( * ) Notice: Subject to any disclaimer, the term of this patent is extended or adjusted under 35 U.S.C. 154(b) by 312 days.

(21) Appl. No.: 09/654,934

(22) Filed: Sep. 1, 2000

Related U.S. Application Data

(63) Continuation-in-part of application No. 09/389,712, filed on Sep. 3, 1999, now Pat. No. 6,143,009, which is a continuation-in-part of application No. 09/241,802, filed on Feb. 2, 1999, now abandoned
(60) Provisional application No. 60/118,611, filed on Feb. 4, 1999.

(51) Int. Cl.$^7$ .............................................. A61B 17/32
(52) U.S. Cl. ..................................................... 606/159
(58) Field of Search ............................... 606/159, 170, 606/167, 180; 604/22

(56) References Cited

U.S. PATENT DOCUMENTS

| | | | | |
|---|---|---|---|---|
| 5,318,576 A | * | 6/1994 | Plassche et al. | 606/159 |
| 6,036,708 A | * | 3/2000 | Sciver | 606/159 |
| 6,312,438 B1 | * | 11/2001 | Adams | 606/159 |
| 6,322,572 B1 | * | 11/2001 | Lee | 606/159 |

* cited by examiner

*Primary Examiner*—A. Vanatta
(74) *Attorney, Agent, or Firm*—Samuel Shiber

(57) ABSTRACT

A rotary flexible agitator system for removing an obstruction from within a patient's vessel comprising a tubular-housing having a flexible-tube with an open distal end, a motor-driven flexible agitator-shaft disposed in the tubular-housing that is rotateable and moveable relative to the flexible-tube. The flexible agitator-shaft has an offset distal-agitator whose effective diameter can be adjusted by pulling or pushing it in or out of the flexible-tube in order to navigate and thread it through obstructions, curved vessels and bifurcations.

16 Claims, 5 Drawing Sheets

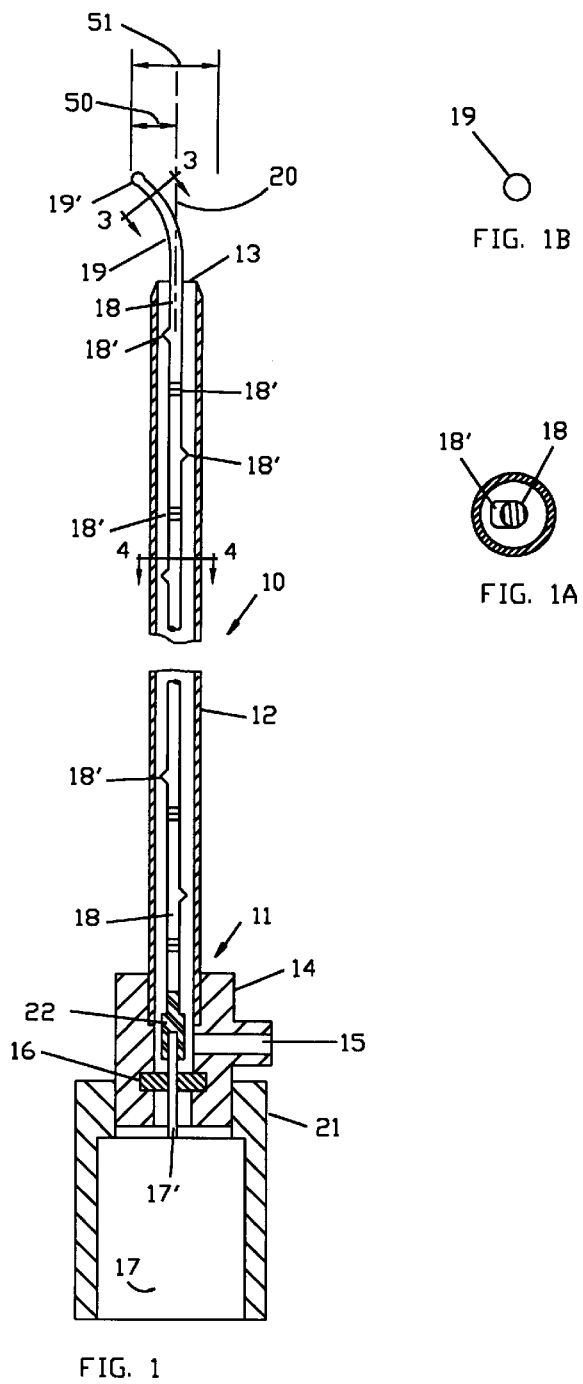
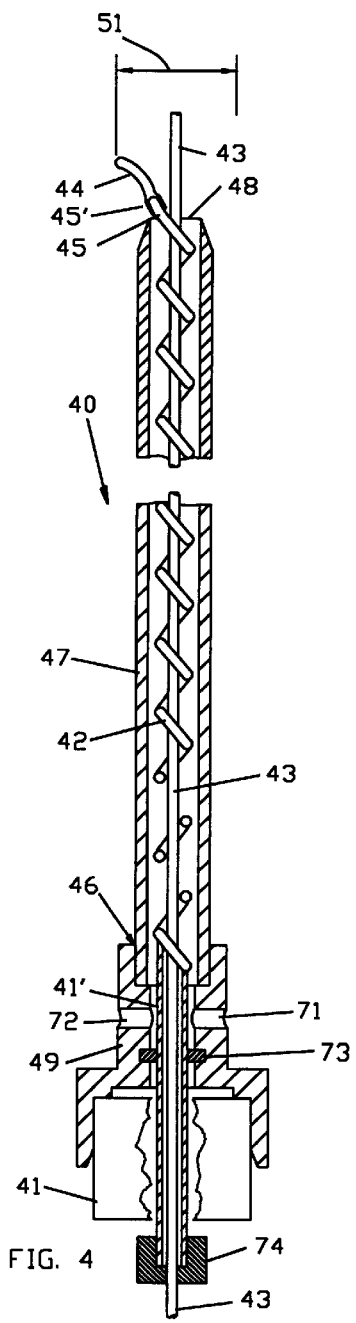
FIG. 1B
FIG. 1A
FIG. 1
FIG. 4

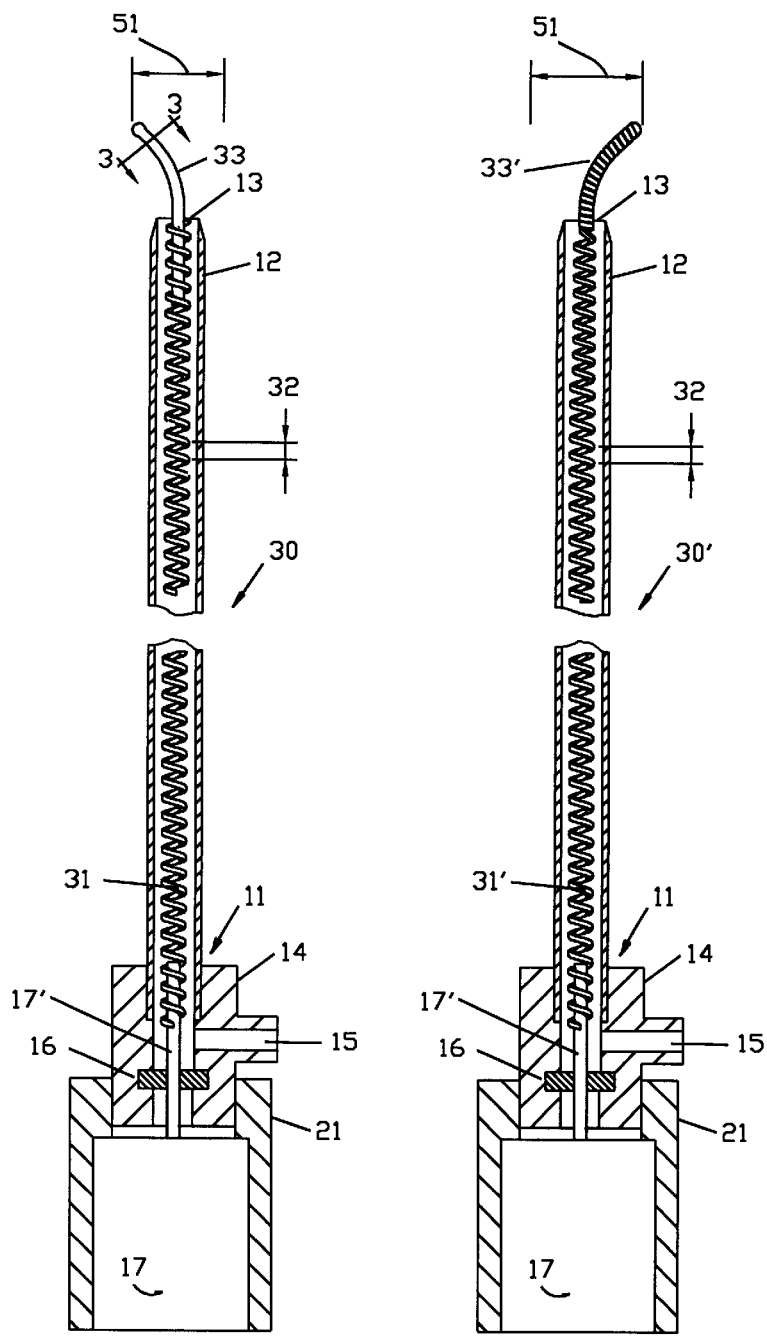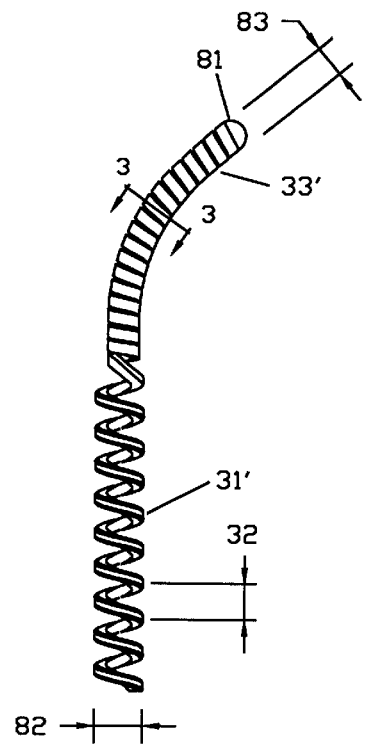
FIG. 3
FIG. 5
FIG. 6

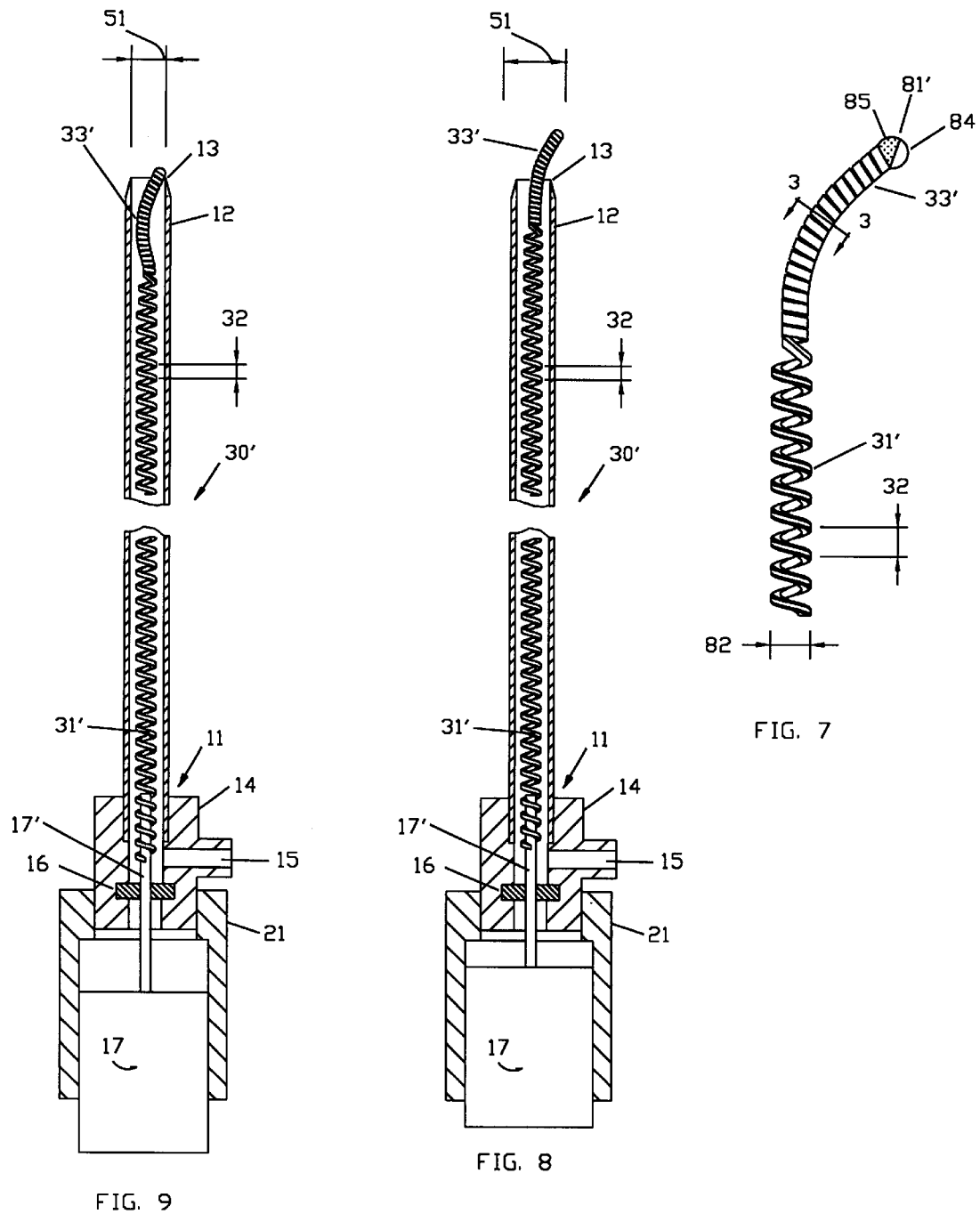

ADJUSTABLE VESSEL CLEANER AND METHOD

CROSS REFERENCE TO OTHER APPLICATIONS

This application is a continuation in part (CIP) of my application Ser. No. 9/389,712 filed on Sep. 3, 1999, now U.S. Pat. No. 6,143,009 that is a CIP of Ser. No. 9/241,802 filed on Feb. 2, 1999, now abandoned. This application also relies for priority on my PCT application PCT/US00/01797 filed on Jan. 25, 2000 that relies for priority on the above applications and on a provisional application Ser. No. 60/118,611 filed on Feb. 4, 1999. All these prior applications are being incorporated herein by reference.

BACKGROUND AND SUMMARY OF THE INVENTION

The rotary flexible-agitator system is designed for removing an obstruction from within a patient's vessel through a tube of small diameter and particularly for opening vessels, such as blood vessels, that tend to become obstructed by thrombi.

Current treatments such as pharmacological, surgical or trans-catheter procedures can be time-consuming, traumatic and expensive. Thus, objects of the present invention are to simplify, improve and shorten the process by enabling the physician to navigate and thread the system through obstructions, curved vessels and bifurcations and then break the obstruction to small pieces that are simultaneously removed through the tube by a combination of suction and mechanical means. These and other objects of the invention will become apparent from the following discussion and the accompanying drawings.

BRIEF DESCRIPTION OF THE FIGURES

FIG. 1 shows a cross-sectional view of a first embodiment of a rotary flexible-agitator system (the midsection of this embodiment and the midsections of the other embodiments are omitted to better fit on the drawing sheet).

FIG. 1A shows a cross-section of an offset distal-agitator as viewed on a cross-sectional plane 4—4 (note FIG. 1). FIG. 1B shows a perimeter of a cross-sectional view as viewed on a cross-sectional plane 3—3 (note FIG. 1).

FIG. 3 shows a cross-sectional view of a second embodiment of a rotary flexible-agitator system.

FIG. 4 shows a cross-sectional view of a fourth embodiment of a rotary flexible-agitator system that is designed to operate over a guidewire.

FIG. 5 shows a cross-sectional view of a third embodiment of a rotary flexible-agitator system that utilizes a flexible agitator-shaft and an offset distal-agitator that are made from a continuous flattened spiral wire.

FIG. 6 shows an enlarged view of the distal portion of the agitator-shaft that is used in the third embodiment The flexible agitator-shaft is made from a flattened wire wound on its edge and an offset distal-agitator that is made from the continuation of the same flattened wire wound on its flat side.

FIG. 7 shows a modified third embodiment where the rounded distal tip is enlarged and a portion of its surface is abrasive.

FIG. 8 shows a cross-sectional view of a third embodiment where the flexible agitator-shaft has been moved relative to the flexible-tube in a proximal direction and has partially pulled the offset distal-agitator into the flexible-tube to adjust its effective diameter.

FIG. 9 shows the same embodiment as in FIG. 8 where the offset distal-agitator has been further pulled into the flexible-tube.

DETAILED DESCRIPTION

Figure 2:
FIG. 2 shows a perspective view of a flat model that is used to explain how the relative motion between a rotary flexible agitator-shaft and a flexible-tube enables the suction to move obstruction pieces through the flexible-tube.

FIG. 1 shows a rotary flexible-agitator system 10 for removing an suction (e.g., thrombus) from within a patients vessel. The system is comprised of a tubular-housing 11 (similar parts shall be denoted by the same numerals throughout the FIGURES) made of a flexible-tube 12 with an open distal end 13 and a proximal end ("distal end" referring to the end that goes further into the vessel and "proximal end" referring to the other end). The proximal end of the tubular-housing defines a port 15 that is connected to the proximal end of the flexible-tube 12. Port 15 can serve as a suction port (suction denotes a pressure lower than the pressure in the vessel that can be used to remove, through the system, fluids and the obstruction pieces from the vessel) or the port 15 can serve as a pressure port to introduce fluids, for example saline with radio-opaque contrast material and heparin, into the vessel. A seal 16 is seated in the proximal end of the tubular-housing.

A motor 17 (e.g., an electric motor, an air-driven turbine or another suitable drive) is conventionally connectable to an appropriate power source (not shown). The motor has an output shaft 17' that fits in and couples to a hollow proximal end 22 of a rotary flexible agitator-shaft 18.

The flexible agitator-shaft is disposed in the tubular-housing and is preferably made from a single piece with a curved, flexible, offset distal-agitator 19 that extends out of the open distal end 13 of the tubular-housing. The curved shape of the offset distal-agitator offsets its rounded end 19' away from the axis 20 of the tube 12 by a distance 50. The cross-section of the offset distal-agitator, whose perimeter is illustrated in FIG. 1B, is sufficiently small and the offset distal-agitator is sufficiently flexible so that it can be inserted through the tube 12 and through a small entry puncture wound in the vessel.

Due to its offset, while the offset distal-agitator rotates its effective diameter 51 is substantially larger than the cross-sectional diameter of the offset distal-agitator or the diameter of the tube 12. Thus, the effective diameter of the agitator is substantially larger than the smallest opening through which the agitator can be inserted. This in turn allows the size of the puncture wound that is required for introducing the system into the vessel (note FIGS. 12 and 13) and the associated trauma to the vessel to be reduced.

A sleeve 21 fits over and aligns the motor 17 with the proximal end 14 and the flexible-tube 12. Alternatively sleeve 21 can be made integral with the proximal end 14.

As the offset distal-agitator breaks the obstruction in the vessel, the pieces are drawn into the open distal end 13 by suction applied to the proximal end of the flexible-tube 12 through the port 15. As the pieces enter the flexible-tube 12 the relative rotational motion between the rotary flexible agitator-shaft and the flexible-tube reduces the friction that inhibits the motion of the pieces through the flexible-tube 12, as explained hereinafter in connection with FIG. 2. This reduction of the friction in the longitudinal direction assists the suction in moving the obstruction pieces through the flexible-tube 12. As the obstruction pieces move through the flexible-tube 12 the relative rotational motion tends to further break down the pieces with protrusions 18', making it easier for the suction to move them through the tubular-housing 11.

FIG. 2 shows a perspective view of a flat model that is used to explain how the relative rotational motion between the agitator-shaft and the flexible-tube is used to reduce the resistance and assist in the movement of obstruction pieces through the flexible-tube.

The model is comprised of a first plane 7 moving in a direction denoted by an arrow 7', a second plane 8 moving in an opposite direction denoted by an arrow 8' and a piece of obstruction 9 that is sandwiched between and frictionally engaged with the planes. Due to these motions full frictional forces develop between the piece 9 and the planes in directions parallel to the arrows 7' and 8'. If at the same time even a small additional force is exerted on the piece 9 in a direction 9' (that is perpendicular to arrows 7' and 8') it will change the direction and size of the overall resultant force acting on the piece and cause its movement in the direction 9'. Absent the above-mentioned relative movement between the planes 7 and 8, the force that would have to be exerted on the piece 9 in order to move it in the direction of arrow 9' would have to be larger than the full frictional force that can develop between the piece 9 and both planes 7 and 8. If plane 7 is envisioned as the outer surface of the flexible agitator-shaft 18 and plane 8 is envisioned as the inside surface of the flexible-tube 12 and the small force in the direction 9' is envisioned to be the force that suction exerts on the obstruction pieces, it can be understood how the relative rotational motion between the flexible agitator-shaft 18 and the flexible-tube 12 assists and enables the suction applied to port 15 to longitudinally move the obstruction pieces through the flexible-tube 12.

FIG. 3 shows a cross-sectional view of a send embodiment of a rotary flexible-agitator system 30 wherein the rotary flexible-agitator comprises a spiral wire 31 (preferably a wire made of metal, e.g. stainless steel, Nitinol or another suitable alloy) that is disposed in the tubular-housing 11. To enhance its flexibility and fatigue resistance the spiral wire is core-less (i.e., it has no central member) except at its two ends. A few of the spiral's proximal coils closely fit over the shaft 17' and are coupled to it, and a few of the spiral's distal coils closely fit over and are coupled to an offset distal-agitator 33, that is preferably made of plastic. As in the other embodiment, the effective diameter of the offset distal-agitator is indicated by numeral 51, and it is substantially larger than the opening of the tube 13.

In addition to agitating the obstruction pieces inside the flexible-tube 12, the spiral serves as a flexible shaft for transmitting rotation and torque from the motor 17 to the offset distal-agitator 33. The linear length of the wire that is used to make the spiral wire 31 is substantially greater than the length of the spiral or of a non-spiral shaft such as a core-wire that could have been placed in the center of the spiral.

Figure 13:
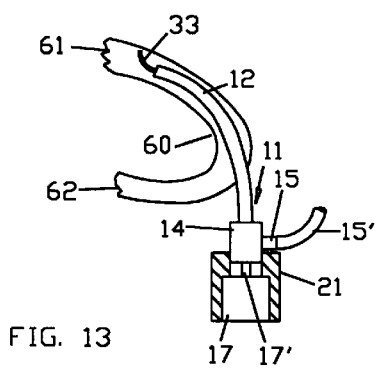
FIG. 13 shows a rotary flexible-agitator system inserted in a U-shaped hemodialysis access graft (shown with its ends severed).
Figure 14:
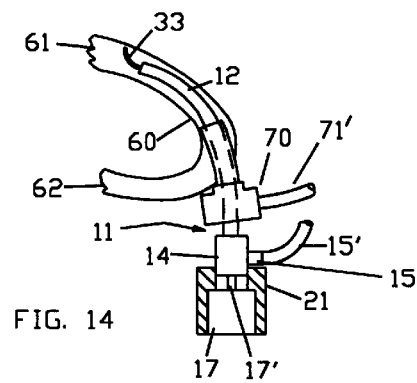
FIG. 14 shows a rotary flexible-agitator system, inserted in a hemodialysis access graft through an introducer. The introducer has a side-arm through which fluid can be delivered into the graft.

The greater linear length of the spiral wire increases the flexibility of the agitator-shaft, and the spiral construction increases its diameter, as compared with a non-spiraled shaft that would have been flexible enough to operate in a curved vessel such as, for example, graft 60 that is illustrated in FIGS. 13 and 14. The increased flexibility of the agitator-shaft 31 reduces the stresses that develop in the wire and its susceptibility to fatigue failure when operating in a curved vessel, as well as the side forces with which the agitator-shaft bears against the flexible-tube 12 and the graft 60. The increased diameter of the agitator-shaft enables the agitator-shaft to radially support the flexible-tube 12 from the inside. Without such support the flexible-tube would tend to kink and diametrically collapse when it is operated in a curved vessel.

FIG. 5 shows a cross-sectional view of a third embodiment of a rotary flexible-agitator system 30', wherein the flexible agitator-shaft 31' and the offset distal-agitator 33' are made from one continuous flattened spiral wire (the narrower side of the 8 flattened wire's cross-section will be referred to as an "edge" and the wider side as a "flat side"). The portion of the wire that makes up the agitator-shaft is wound on its edge as illustrated in FIG. 6. This further increases the flexibility and torque carrying capacity of the agitator-shaft (as compared to a spiral wound from a round wire with the same cross-sectional area). The portion of the wire that makes up the offset distal-agitator is wound on its flat side. This reduces the gap between the coils and the likelihood of material being caught between them, and it also lends itself to manufacturing the agitator-shaft with a cross-sectional diameter 82 that is larger than the offset distal-agitator's cross-sectional diameter 83 which in turn leaves more of the distal end 13 open for the pieces to enter the flexible-tube 12. The distal tip 81 of the offset distal-agitator is rounded (note FIG. 6) to reduce the trauma that it might impart on the vessel.

The motor's shaft 17' is preferably rotated in a direction so that the relative motion between the spiral and the flexible-tube 12 mechanically assists the suction applied to port 15 in conveying the obstruction material into the open distal end 13 and through the flexible-tube 12. However, since the flow through the tube is not synchronized with the rate of advancement of the spiral wire's coils (which is the product of the spiral's rotational speed multiplied by the spiral's pitch 32), the relative motion between the rotating flexible agitator-shaft and the flexible-tube 12 further breaks the pieces as they pass through the flexible-tube 12.

When the motor's direction of rotation is reversed the mechanical pumping action of the spiral is also reversed and opposes the suction in moving the obstruction material through the flexible-tube 12. However, by increasing the spacing between the spiral and the wall of the flexible-tube 12, or by changing the pitch of the spiral, the mechanical pumping action of the spiral can be adjusted so that the suction applied at the port 15 will dominate the direction of the flow through the flexible-tube 12. While the reversal of the mechanical pumping action reduces the rate of flow through the flexible-tube 12, it increases the opportunity of the obstruction pieces to collide with the rotating spiral and be further broken down. Optionally, the motor can be periodically, manually or automatically, reversed to assist in releasing pieces of the obstruction that may have become stuck in the flexible-tube 12 or wrapped around the agitator. (This technique is applicable to any of the embodiments.)

As in the other embodiments, the relative rotational motion between the flexible agitator-shaft and the flexible-tube 12 assists the suction applied to port 15 to longitudinally move the obstruction pieces through the flexible-tube.

FIG. 7 shows a modified third embodiment where the rounded distal tip 81' is made larger, and a portion of its surface 84, orientated so that it is more likely to come in contact with the vessel's wall, is smooth. The other portion of its surface 85 is made abrasive by, for example, forming on it or bonding to it small protrusions.

FIG. 8 shows a cross-sectional view of the third embodiment where the motor 17 together with the flexible agitator-shaft 31' are shown moved relative the flexible-tube 12 in a proximal direction and they have partially pulled the offset distal-agitator 33' into the flexible-tube and thereby adjusted its effective diameter 51 to become smaller.

FIG. 9 shows the same embodiment of FIG. 8 where the offset distal-agitator has been further pulled into the flexible-tube.

Figure 10:
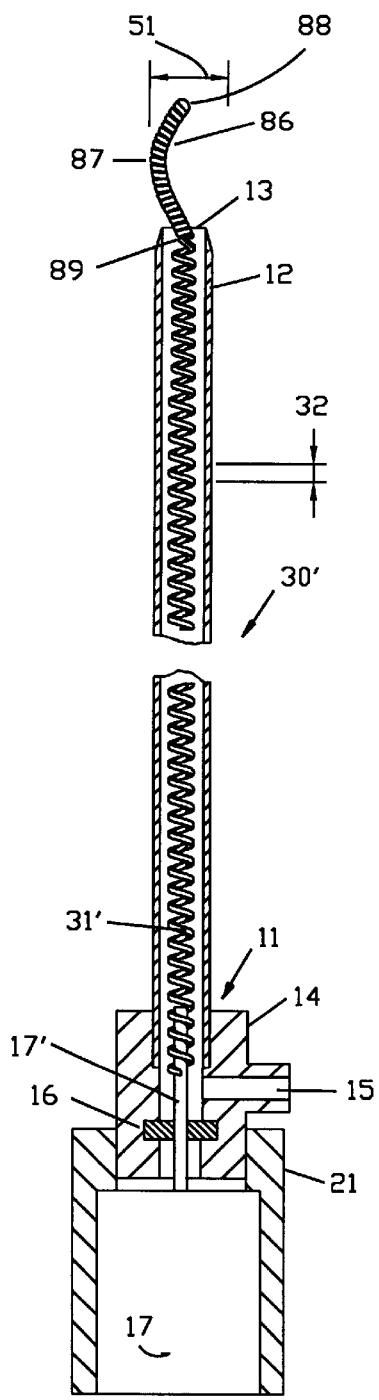
FIG. 10 shows a cross-sectional view of a fifth embodiment of a rotary flexible-agitator system that utilizes a flexible agitator-shaft and an offset distal-agitator that are made from a continuous flattened spiral wire. The flexible agitator-shaft is made from a flattened wire wound on its edge and an offset distal-agitator that is made from the continuation of the same flattened wire wound on its flat side
Figure 11:
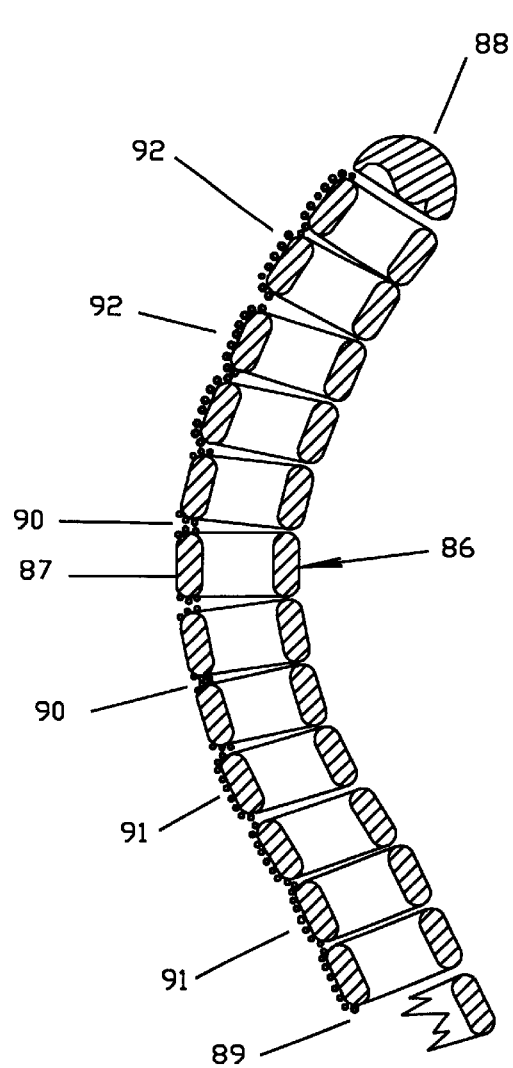
FIG. 11 shows an enlarged view of a modified offset distal-agitator of the fifth embodiment where a portion of its surface is abrasive.

FIGS. 10 and 11 show a cross-sectional view of a fifth embodiment wherein the offset distal-agitator 86 is shaped so that its distance from the longitudinal axis of the tube 12 is largest at a point 87 that is located between the offset distal-agitator's rounded tip 88 and its proximal end 89. This reduces the likelihood that the rounded tip 88 will inadvertently enter a side-branch or a hole in the vessel's wall. As in the other embodiments, the effective diameter 51 of the offset distal-agitator is substantially larger than its cross-sectional diameter and it also can be adjusted by pulling it into the flexible tube 12.

FIG. 11 shows, on a larger scale, an offset distal-agitator of the fifth embodiment with an optional modification that enables it abrade the obstruction material. Since the distance of the offset distal-agitator from the longitudinal axis of the tube 12 is largest at a point 87 the surface of the offset distal-agitator around this point is more likely to come in contact with the vessel's wall and therefore it is preferably made smooth to minimize trauma to the vessel, however other surfaces of the offset distal-agitator 91 and 92 as well as the spaces between the spiral windings 90 can, optionally, be made abrasive by forming or bonding to them small protrusions which are symbolically represented by small black circles on FIG 11. The protrusions can also be applied selectively to surface 91 for abrading an obstruction primarily while moving the system in the vessel proximally or they can be applied selectively to surface 92 for abrading an obstruction while moving in a distal direction in the vessel.

FIG. 4 shows a cross-sectional view of a fourth embodiment of a rotary flexible-agitator system 40. In this embodiment the shaft 41' of the motor 41 is a tube, that together with a spiral 42, which is affixed and coupled to the tube's distal end, defines a continuous passageway that can accommodate a guidewire 43 or a similar elongated object (e.g., an optic fiber or an ultrasound probe). The spiral wire 42 is also preferably made of a metal wire, and its distal end 45 is affixed to a hollow end 45' of an offset distal-agitator 44.

The fourth embodiments tubular-housing 46 is made of a flexible-tube 47 with an open distal end 48 and a proximal end 49 which defines a suction port 71, that is connected to the proximal end of the flexible-tube 47. An optional second port 72 can be used to introduce fluid into the proximal end 49. Such fluid can be used to dilute the slurry of obstruction pieces that is removed through port 71. A seal 73, seated in the proximal end of the tubular-housing, minimizes leakage around the motor shaft. A seal 74, that is attached to the proximal end of the shaft 41', minimizes leakage around the guidewire 43 and through the shaft 41'. The proximal end 49 defines an open cylinder that fits around the motor 41 and concentrically aligns the motor with the flexible-tube 47.

Figure 12:
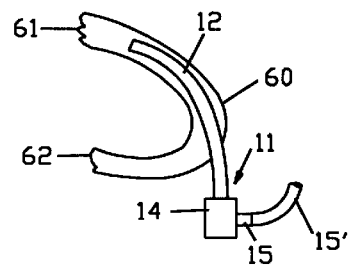
FIG. 12 shows a tubular-housing inserted in a U-shaped hemodialysis access graft (shown with its ends severed).

FIG. 12 shows the tubular-housing 11 inserted in a vessel such as a U-shaped hemodialysis access graft 60 (the graft's ends, 61 and 62, are normally connected to a vein and an artery neither of which is shown).

FIG. 13 shows a rotary flexible-agitator system where an offset distal-agitator 33 is connected to a flexible agitator-shaft that is disposed (and hidden) in the tubular-housing 11 and is connected to a motor's shaft 17'.

FIG. 14 shows the rotary flexible-agitator system, inserted in a hemodialysis access graft 60 through an introducer 70 ("introducer" denotes a device that is used to introduce another device into the vessel, for example, a commercially available introducer sheath, a guiding catheter, etc.) with its own side-arm 71', through which fluid can be introduced into the graft.

Operation

After the rotary flexible-agitator system is inserted into a vessel, directly as shown in FIG. 13 or through an introducer as shown in FIG. 14, the system is advanced distally into the vessel. When its advance is hampered by an obstruction, a sharp curve in the vessel, or when it veers to the wrong side of a bifurcation the physician can back the system and adjust the effective diameter by pulling or pushing the offset distal-agitator so that it moves into or out of the flexible-tube and the interaction between the offset distal-agitator and the flexible-tube causes the effective diameter to change (note FIGS. 8 and 9). In addition, while adjusting the effective diameter the physician can rotate, manually or by activating the motor 17 in either direction preferably at a low speed, the offset distal-agitator to further assist in passing various obstacles. While advancing in the vessel, radio-opaque fluid and medication can be delivered into it through the introducer 70 and additionally through the port 15 which connects to the flexible-tube 12, to facilitate imaging the procedure The advantage of the flexible-tube is that it delivers the radio-opaque fluid to a more distal section of the vessel which the introducer does not reach.

After passing the obstruction, and prior to activating the motor, the delivery of fluid to the vessel through the flexible tube is stopped and instead suction is applied to the flexible-tube. Then the motor is activated and the system is moved proximally while the rotating offset distal-agitator breaks and/or abrades the obstruction to pieces. Simultaneously, the suction pulls the pieces into the distal opening 13 of the flexible-tube where, together with the mechanical action of the flexible agitator-shaft, it evacuates the obstruction particles from the patient's body.

Alternatively the motor can be activated before passing the obstruction and the system can be activated while advancing distally into the vessel.

As can be seen, it is an objective of this invention to provide a simple, reliable his and cost effective system that combines features of a steerable catheter and a thrombectomy device that can be introduced into a vessel through a small minimally traumatic opening, to enable distal delivery of radio-opaque fluid to enhance imaging and to remove the obstruction particles through the small opening in the vessel.

It should be understood that various modifications and substitutions may be made to the system and to the method of using it without departing from the spirit of the invention or the scope of the claims.

I claim:

1. A rotary flexible agitator system for removing an obstruction from within a patient's vessel comprising in combination:
   a tubular-housing having a flexible-tube with an open distal end,
   a motor-driven flexible agitator-shaft disposed in the tubular-housing, the flexible agitator-shaft being rotateable and moveable relative to the flexible-tube,
   the flexible agitator-shaft having an offset distal-agitator that extends out of the open distal end of the flexible-tube to break the obstruction to pieces while rotating with an effective diameter that is larger than its cross-sectional diameter,
   wherein the flexible agitator-shaft is moveable relative to the flexible-tube to thereby pull or push the offset distal-agitator in or out of the flexible-tube and thereby adjust the effective diameter of the offset distal-agitator.

2. As in claim 1 wherein the agitator-shaft comprises a spiral wire.

3. As in claim 2 wherein the spiral wire radially supports the flexible-tube while the rotary agitator system is operated in a curved vessel.

4. As in claim 1 wherein the agitator-shaft and the offset distal-agitator are made from a continuous spiral wire.

5. As in claim 4 wherein the agitator-shaft is made of a flattened wire wound on its edge and the offset distal-agitator is made from the same flattened wire wound on its side.

6. As in claim 2, 3, 4 or 5, wherein the spiral wire is core-less.

7. As in claim 1, wherein the cross-sectional diameter of the agitator-shaft is larger than the cross-sectional diameter of the offset distal-agitator.

8. As in claim 1 wherein the flexible-tube is curved.

9. As in claim 1 wherein a portion of a surface of the offset distal-agitator that comes in contact with the vessel's wall is smooth, and another portion of the surface is abrasive.

10. As in claim 1 wherein the rotary flexible agitator-shaft has radial protrusions that, during the relative motion between the rotary flexible agitator-shaft and the flexible-tube, further break the pieces as they pass through the flexible-tube.

11. A method of steering a medical apparatus having a flexible-tube in which a motor-driven flexible agitator-shaft is disposed in and is connected to an offset distal-agitator that extends out of an open distal end of the tube, comprising the following steps:
   inserting the apparatus into a vessel,
   advancing the apparatus distally in the vessel until an obstacle is encountered,
   adjusting the effective diameter by pulling or pushing the offset distal-agitator into or out of the flexible-tube to adjust the effective diameter to facilitate steering it past the obstacle.

12. A method for unclogging a vessel with an apparatus having a flexible-tube in which a motor-driven flexible agitator-shaft is disposed, and the flexible agitator-shaft is connected to an offset distal-agitator that extends out of an open distal end of the tube, comprising the following steps:
   inserting the apparatus into the vessel,
   advancing the apparatus distally in the vessel until an obstacle is encountered,
   adjusting the effective diameter by pulling or pushing the offset distal-agitator into or out of the flexible-tube to facilitate passing the offset distal-agitator through the obstruction,
   activating the motor to rotate the flexible agitator-shaft and the offset distal-agitator while moving them proximally in the vessel so that the offset distal-agitator that extends out of the open distal end of the flexible-tube breaks the obstruction to pieces.

13. As in claim 11 or 12, wherein the offset distal-agitator is rotated to further facilitate steering it past the obstacle.

14. As in claim 11 or 12, wherein radio-opaque fluid is delivered to the distal end of the apparatus though the flexible-tube to assist in imaging the vessel.

15. As in claim 11 or 12, wherein the rotary flexible-agitator system is inserted into the vessel through an introducer.

16. As in claim 11 or 12, wherein the rotary flexible-agitator system is inserted into the vessel through an introducer through which fluids can be introduced into the vessel.

* * * * *